United States Patent [19]
Okawa et al.

[11] Patent Number: 5,999,004
[45] Date of Patent: *Dec. 7, 1999

[54] METHOD OF DETECTING A CHANGE IN THE PROPERTY OF A RUBBER MEMBER

[75] Inventors: Yoshinao Okawa; Youichi Akutsu, both of Ibaraki; Ikuo Shimoda; Masayoshi Ikenaga, both of Fujisawa, all of Japan

[73] Assignee: Japan Atomic Energy Research Insittute, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/694,921
[22] PCT Filed: Jun. 29, 1994
[86] PCT No.: PCT/JP94/01048
§ 371 Date: Feb. 1, 1995
§ 102(e) Date: Feb. 1, 1995
[87] PCT Pub. No.: WO95/01564
PCT Pub. Date: Jan. 12, 1995

Related U.S. Application Data

[63] Continuation of application No. 08/379,591, Feb. 1, 1995, abandoned.

[30] Foreign Application Priority Data

Jun. 30, 1993 [JP] Japan .................................. 5-188742

[51] Int. Cl.[6] .................................................. G01R 27/08
[52] U.S. Cl. .......................... 324/717; 248/632; 248/638; 52/167.8; 324/541; 324/691
[58] Field of Search ...................................... 324/717, 557, 324/541, 691, 722; 606/34; 52/167.7, 167.8, 167.9; 248/632, 638

[56] References Cited

U.S. PATENT DOCUMENTS

| | | | |
|---|---|---|---|
| 4,667,519 | 5/1987 | Burg | 73/815 |
| 4,720,669 | 1/1988 | Owen | 324/557 |
| 4,800,751 | 1/1989 | Kobayashi et al. | 73/628 |
| 4,980,645 | 12/1990 | Soma et al. | 324/541 |
| 5,045,829 | 9/1991 | Kuramochi et al. | 73/862.625 |
| 5,389,097 | 2/1995 | Bennett et al. | 606/34 |

FOREIGN PATENT DOCUMENTS

| | | |
|---|---|---|
| A-0 312 623 | 4/1989 | European Pat. Off. . |
| 61-33368 | 8/1986 | Japan . |
| 64-10775 | 2/1989 | Japan . |
| 2-500998 | 4/1990 | Japan . |
| 2-35850 | 10/1990 | Japan . |
| A-04 147024 | 5/1992 | Japan . |

Primary Examiner—Josie Ballato
Assistant Examiner—Thomas Valone
Attorney, Agent, or Firm—Nixon & Vanderhye

[57] ABSTRACT

The electrical impedance of a dumbbell-shaped rubber sheet (1) is measured, and the deterioration of the dumbbell-shaped rubber sheet (1) is detected from the result of the measurement. The present invention relates to a method of detecting a change in the property of a rubber member or a rubber member of a rubber bearing, such as a change in the shape or dimensions thereof, a change in the state of the stress and strain thereof, deterioration thereof, and the like.

6 Claims, 7 Drawing Sheets

METHOD OF DETECTING A CHANGE IN THE PROPERTY OF A RUBBER MEMBER

This is a continuation of application Ser. No. 08/379,591, filed Feb. 1, 1995, now abandoned.

TECHNICAL FIELD

The present invention relates to a method of detecting a change in the property of a rubber member or a rubber member of a rubber bearing, such as a change in the shape or dimensions thereof, a change in the state of stress and strain thereof, deterioration thereof, and the like.

BACKGROUND ART

A rubber bearing which is comprised of a rubber member and a reinforcing member is used in supporting a structure such as a building and the like. As a result of the fact that such rubber bearings are generally disposed in a lower portion of the structure, the rubber bearings receive the load of the structure over a long period of time, and are also subjected to shear stress due to earthquakes and the like, while they gradually deteriorate due to aging or the like. When the deterioration of a fixed level or more has occurred, it is necessary to replace the rubber bearings, and the extent of the deterioration of the rubber member of the rubber bearing is conventionally ascertained by visual observation of a configuration or dimensional change in the overall configuration of the rubber member, a crack or an exfoliation in the rubber member or the like, or by the use of a measuring instrument such as a strain gauge, an ultrasonic test instrument, or a measure.

Since the rubber bearings are generally disposed in a lower portion of the structure as described above, the visual observation of the rubber members is very difficult since an inspector must enter the lower portion of the structure and conduct the visual observation. In addition, the inspector must rely on his experience and intuition in the observation, so that there is a possibility that the results of observation may vary. Meanwhile, in the observation of the rubber members by the use of measuring instruments such as those described above, it is possible to obtain satisfactory results to a certain extent when a dimensional change is involved. When a dimensional change is not involved, it is impossible to obtain desired results. In order to monitor the supporting performance of the rubber bearings during the period of use, it is necessary to remove the rubber bearings from the structure, or separately prepare in advance a rubber bearing specimen of the same material as that of the rubber bearings installed under the structure, and to conduct a dynamic test by applying a fixed axial force to the rubber bearing specimen after the lapse of a predetermined period. Thus, it has been impossible to monitor the supporting performance of the rubber bearings in use as installed under the structure.

Such a problem occurs not only with the rubber member itself of the rubber bearing, but, generally speaking, it can similarly occur with rubber members applied to various members which are formed of material such as natural rubber, synthetic rubber, or the like.

The present invention has been devised in view of the above-described aspects, and its object is to provide a method of detecting a change in the property of a rubber member, the method being capable of reliably observing the extent of deterioration even when a dimensional change is not involved, and in the case of a rubber member of a rubber bearing, making it unnecessary for an inspector to enter a lower portion of a structure at the time of observation, and making it possible to reliably ascertain the extent of deterioration remotely.

DISCLOSURE OF INVENTION

In accordance with the present invention, the above-described object is attained by a method comprising the steps of: measuring an electrical impedance of a rubber member; and detecting a change in a property of the rubber member from a result of the measurement.

In addition, the above object is also attained by a method comprising the steps of: measuring an electrical impedance of a rubber member of a rubber bearing which comprises the rubber member and a reinforcing member; and detecting a change in a property of the rubber member of the rubber bearing from a result of the measurement.

Here, in a case where the reinforcing member is made of a metal, the electrical impedance of the rubber member may be measured by using the reinforcing member as an electrode. Furthermore, in a case where the rubber bearing further has flange plates respectively disposed on opposite end surfaces of the rubber member, the electrical impedance of the rubber member may be measured by using the flange plates as electrodes.

The changes of the properties which can be detected by the present invention include a dimensional change, a change in the state of stress and strain, deterioration, and the like, and it is possible to cite the deterioration, in particular.

The material of the rubber member, which is the object to be measured in the present invention, may be natural rubber, synthetic rubber, or a mixture thereof. In the case of the rubber bearing which is used in an earthquake-resistant device, an isolator, and a vibration-control device, there are cases where high-damping rubber is used, and the method of the present invention can be suitably applied to the rubber member made of such a high-damping rubber. The rubber bearing used in the earthquake-resistant device, the isolator, and the vibration-control device is formed with a lead plug additionally disposed in the center of the rubber member, as necessary, and the method of the present invention can be suitably applied to such a rubber bearing incorporating the lead plug.

In the present invention, electrodes are disposed such that the rubber member whose change in the property is to be detected is placed therebetween. A voltage of, for instance, 200 kHz is applied across these electrodes, and the electrical impedance of the rubber member is measured from a current value. Here, the electrical impedance changes in correspondence with the change in the property of the rubber member, e.g., the generation of the internal strain, so that the change in the property of the rubber member can be detected from the result of the measurement.

As described above, in accordance with the present invention, even when a dimensional change is not involved, it is possible to reliably observe the extent of deterioration of the rubber member, and, in the case of a rubber bearing, it is unnecessary for an inspector to enter a lower portion of the structure at the time of observation, and it is possible to reliably ascertain the extent of deterioration remotely.

Hereafter, a description will be given of the present invention with reference to the embodiments shown in the drawings. It should be noted that the present invention is not limited to these embodiments.

EMBODIMENTS

EXAMPLE 1

Figure 1:
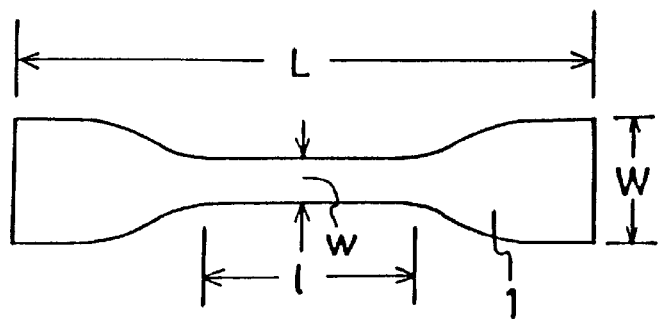
FIG. 1 is a plan view of a rubber sheet used in Example 1 for explaining the method of the present invention.
Figure 2:
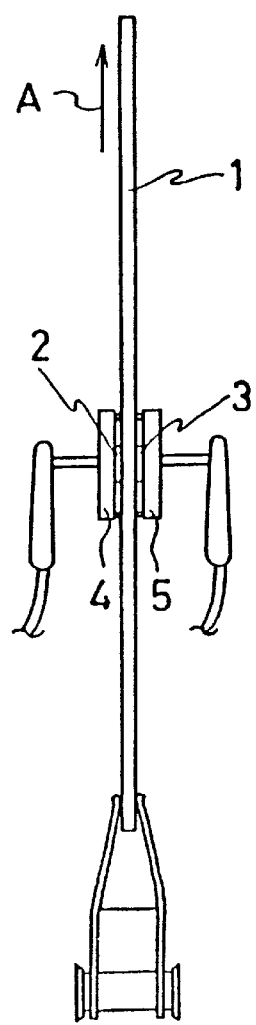
FIG. 2 is a front elevational view explaining a measuring method in accordance with Example 1.

A dumbbell-shaped rubber sheet 1 of No. 1 type of JIS (K6301) such as the one shown in FIG. 1 was prepared as an object to be measured. As for this rubber sheet 1 as a rubber member, its overall length L was 120 mm, the length l of its small-width portion was 40 mm, the width W of its large-width portion was 25 mm, the width w of its small-width portion was 10 mm, and its thickness t was 2 mm. Then, as shown in FIG. 2, electrodes 2 and 3, which were formed of copper plates having a diameter of 5 mm and a thickness of 1 mm, were applied to both sides of the rubber sheet 1, and they were clamped and held by polyethylene plates 4 and 5. Under the conditions of the temperature: 25° C., a deformation rate: 10 mm/min, and a pressing force: 3 windings, an elongating force in the direction of arrow A (in the longitudinal direction) was applied to this rubber sheet 1 repeatedly four times such that the elongation percentage (100%=50 mm) became 0%-25%-0%-50%-0%-75%-0%-100%-0%. At the same time, a voltage with a frequency of 200 kHz was applied across the electrodes 2 and 3. The results of measurement are shown in FIGS. 3 to 6.

Figure 3:
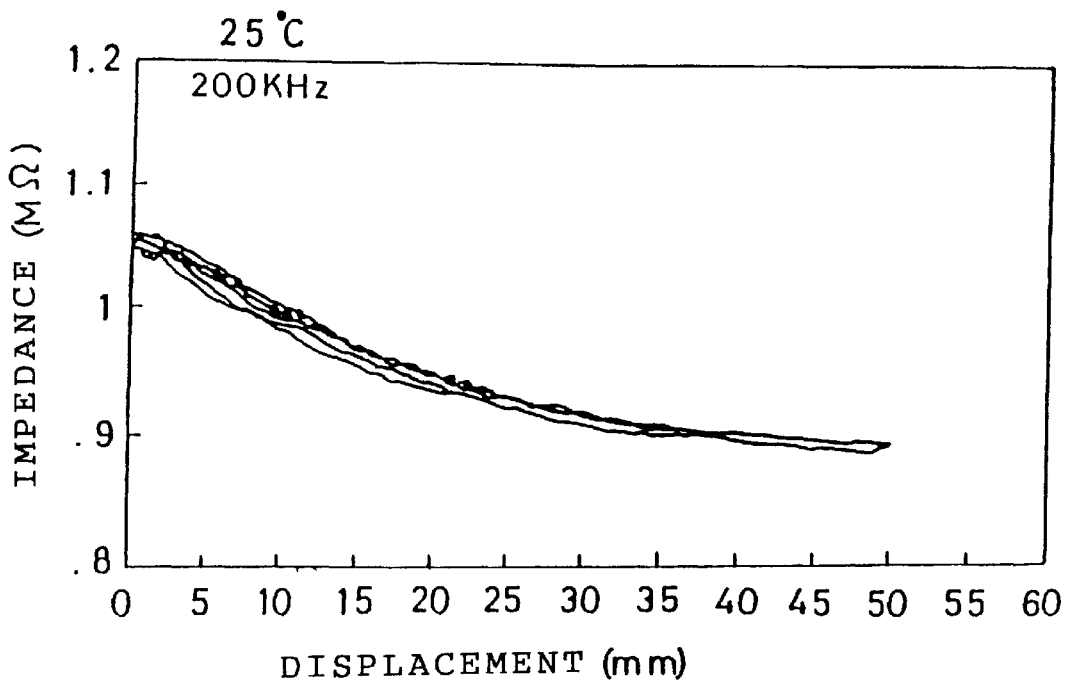
FIG. 3 is the result of measurement of the relationship between the displacement of the rubber sheet and the impedance between electrodes in Example 1.
Figure 4:
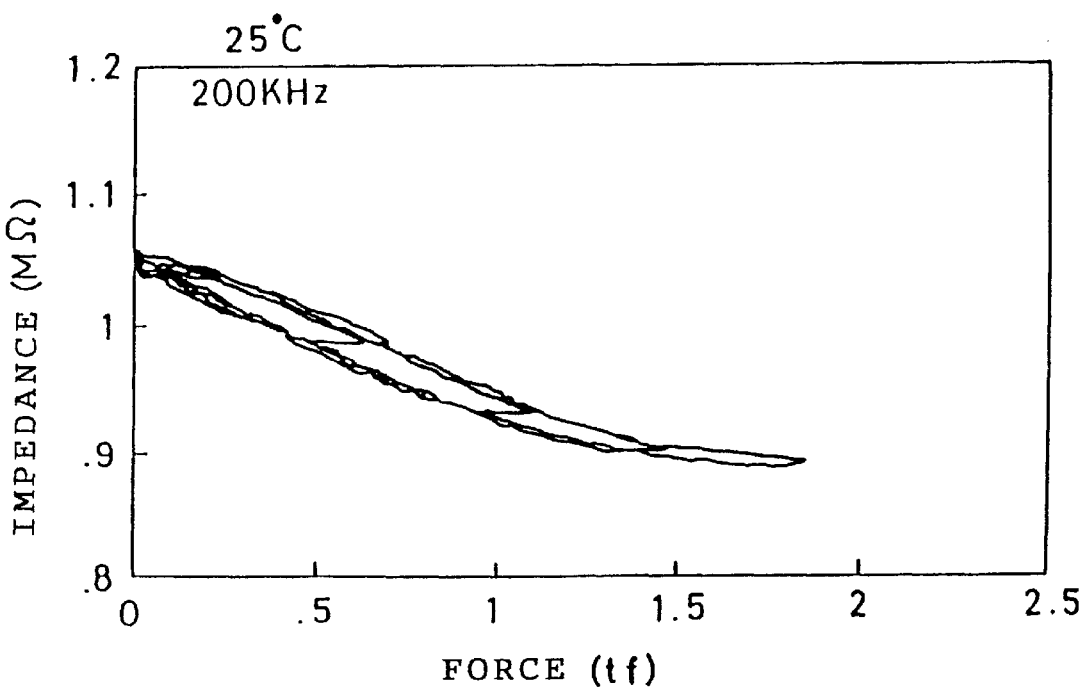
FIG. 4 is the result of measurement of the relationship between a force applied to the rubber sheet and the impedance between the electrodes in Example 1.
Figure 5:
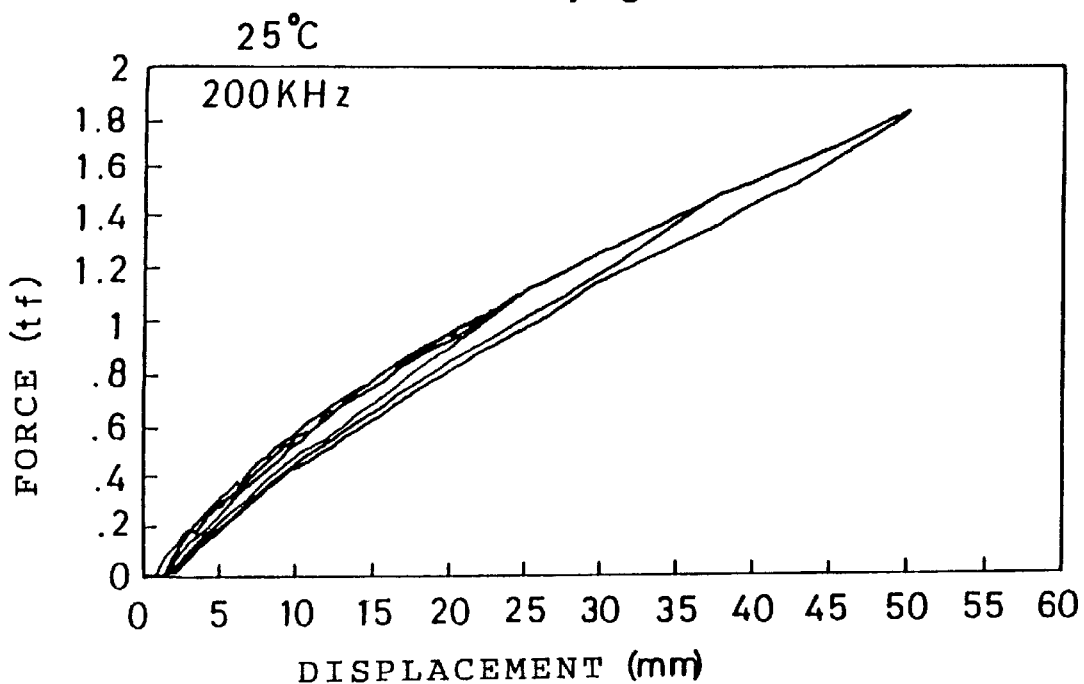
FIG. 5 is the result of measurement of the relationship between the displacement of the rubber sheet and the force applied to the rubber sheet in Example 1.
Figure 6:
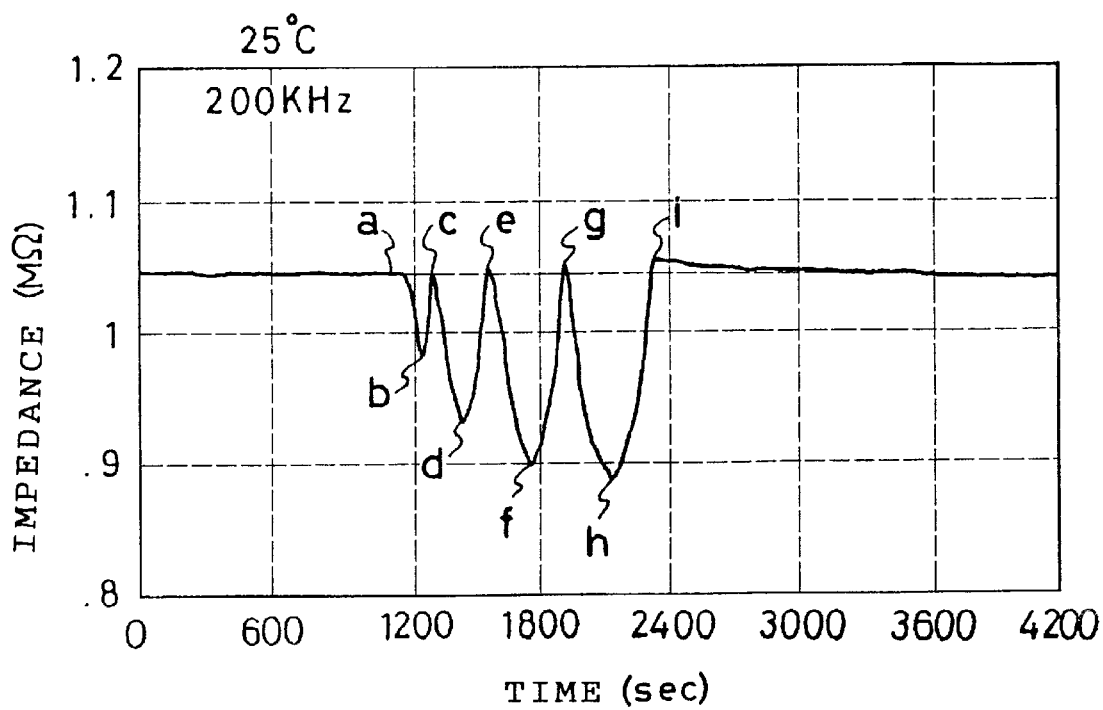
FIG. 6 is the result of measurement of the relationship between the elapsed time and the impedance between the electrodes in Example 1.

Here, FIG. 3 shows the result of measurement of the relationship between the displacement of the rubber sheet 1 and the impedance between the electrodes 2 and 3. FIG. 4 shows the result of measurement of the relationship between the force applied to the rubber sheet 1 and the impedance between the electrodes 2 and 3. FIG. 5 shows the result of measurement of the relationship between the displacement of the rubber sheet 1 and the force applied to the rubber sheet 1. FIG. 6. shows the result of measurement of the relationship between the elapsed time and the impedance between the electrodes 2 and 3. Incidentally, as the measuring instrument, the LF Impedance Analyzer (Model 4129A manufactured by Yokogawa-Hewlett-Packard, Ltd.) was used.

Figure 7:
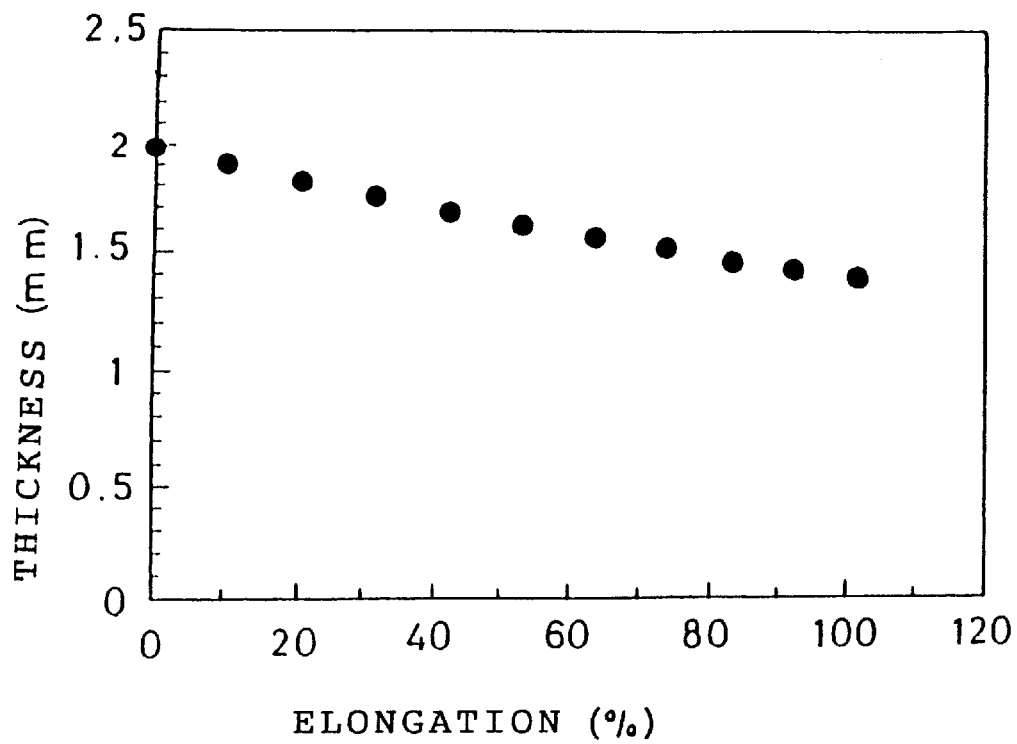
FIG. 7 is the result of measurement of the relationship between the elongation and the thickness in Example 1.

Focusing attention on FIG. 6, it can be seen that the impedance changes in the order of a, b, c, d, e, f, g, h, and i in correspondence with the application of the elongating force of 0%-25%-0%-50%-0%-75%-0%-100%-0%. Also, it can be seen that the impedances c, e, g, and i are respectively greater than the original impedance a, and that the impedance gradually increases in the order of c, e, g, and i in correspondence with an increase in the number of times the elongating force is applied. Accordingly, by detecting the change in impedance from the original impedance, it is possible to detect the application of the elongating force to the rubber sheet 1, i.e., the occurrence of the internal strain in the rubber sheet 1. In addition, by detecting the amount of increase in impedance, it is possible to detect the extent of deterioration of the rubber sheet 1 ascribable to the generation of the repeated internal strains. The large changes exhibited by the impedances b, d, f, and h are conceivably attributable to the changes in the thickness of the rubber sheet 1 due to the elongation. For reference, FIG. 7 shows the result of measurement of the relationship between elongation and thickness.

EXAMPLE 2

Figure 8:
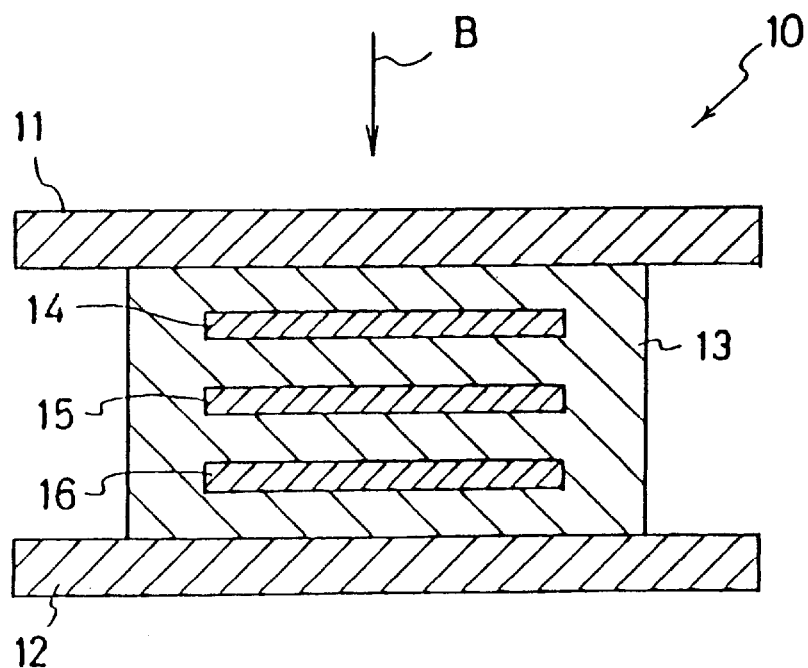
FIG. 8 is a cross-sectional view of a rubber bearing used in Example 2 for explaining the method of the present invention.

A rubber bearing 10 such as the one shown in FIG. 8 was prepared. The rubber bearing 10 is comprised of disk-shaped upper and lower connecting steel plates (upper and lower flange plates) 11 and 12, a cylindrical rubber member 13, and three disk-shaped inner steel plates 14, 15, and 16 serving as reinforcing members embedded in the rubber member 13. Lead wires are respectively screwed to the inner steel plates 14 and 15 of the rubber bearing 10, the lead wires were led to the outside, and the inner steel plates 14 and 15 were used as electrodes. Under the temperature condition of 23° C., a uniform stationary compressive force with a surface pressure of 40 kgf/cm$^2$ and a load of 4.46 tonf was applied to the rubber bearing 10 repeatedly three times in the direction of arrow B (in the vertical direction). At the same time, a voltage with a frequency of 100 kHz was applied across the inner steel plates 14 and 15. The results of measurement are shown in FIGS. 9 to 12.

Figure 9:
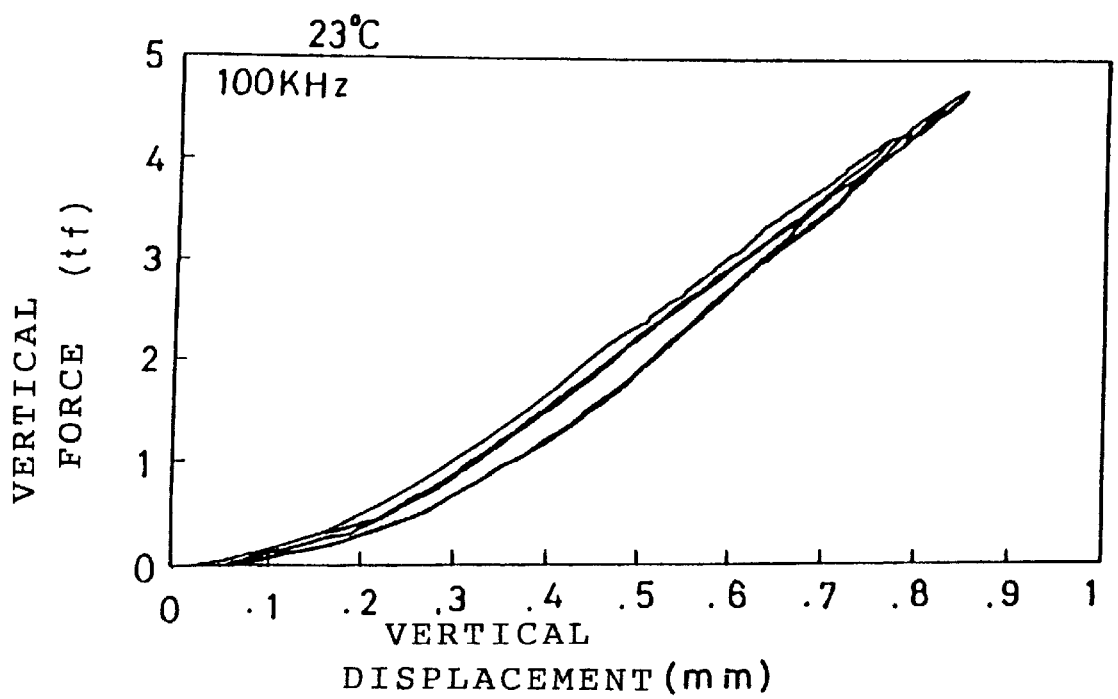
FIG. 9 is the result of measurement of the relationship between a vertical displacement occurring to the rubber member and a vertical force applied to the rubber member in Example 2.
Figure 10:
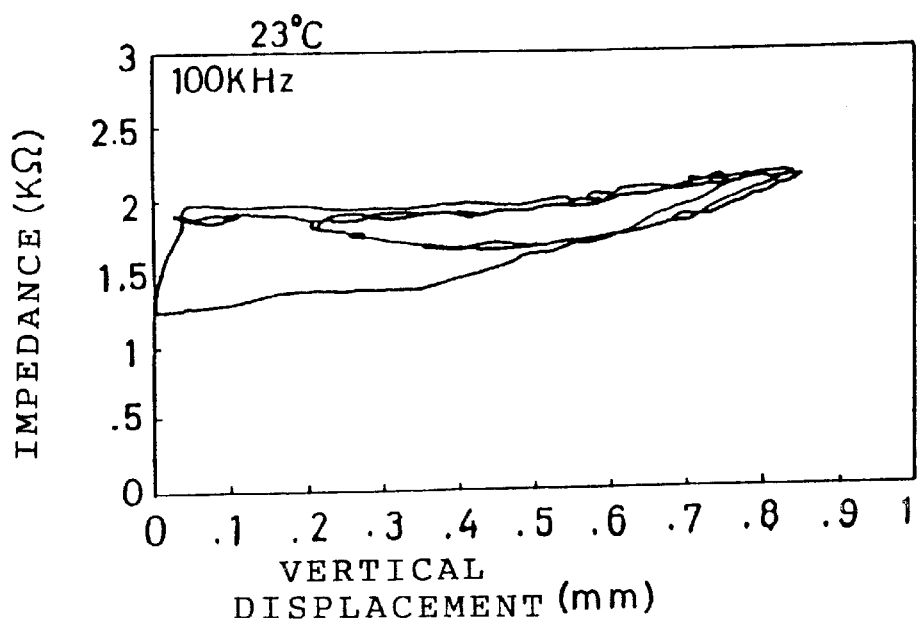
FIG. 10 is the result of measurement of the relationship between the vertical displacement occurring to the rubber member and the impedance between inner steel plates in Example 2.
Figure 11:
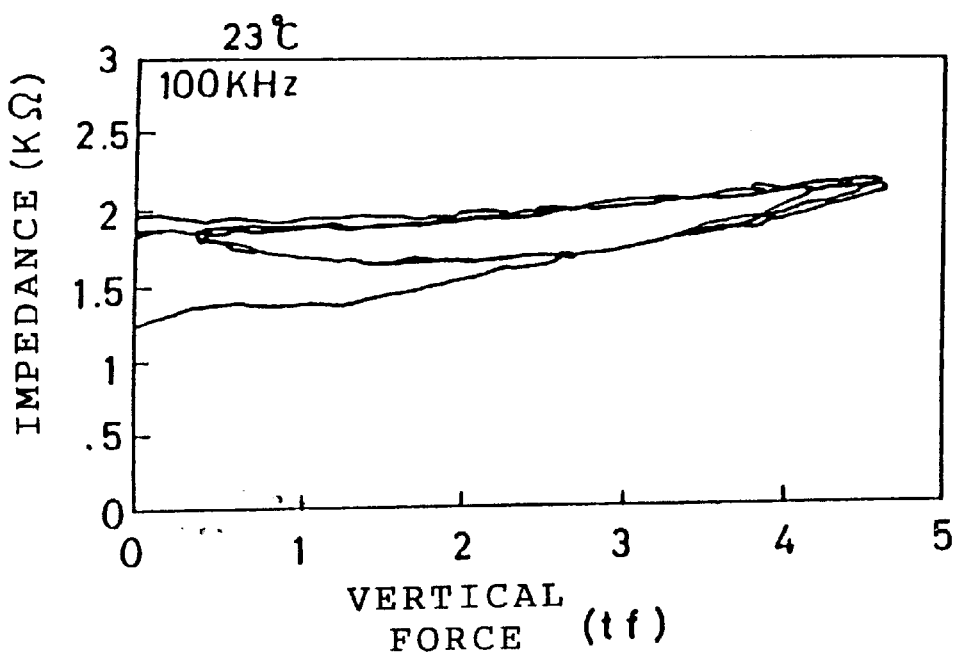
FIG. 11 is the result of measurement of the relationship between a vertical force applied to the rubber member and the impedance between the inner steel plates in Example 2.
Figure 12:
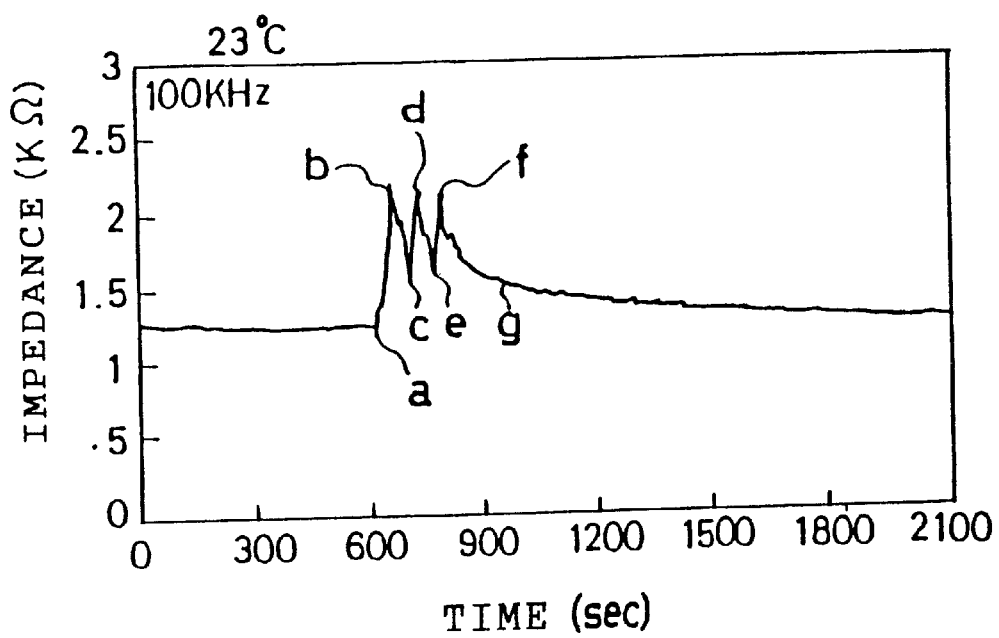
FIG. 12 is the result of measurement of the relationship between the elapsed time and the impedance between the electrodes in Example 2.

FIG. 9 shows the result of measurement of the relationship between the vertical displacement occurring in the rubber member 13 and the vertical force applied to the rubber member 13. FIG. 10 shows the result of measurement of the relationship between the vertical displacement occurring in the rubber member 13 and the impedance between the inner steel plates 14 and 15. FIG. 11 shows the result of measurement of the relationship between the vertical force applied to the rubber member 13 and the impedance between the inner steel plates 14 and 15. FIG. 12 shows the result of measurement of the relationship between the elapsed time and the impedance between the inner steel plates 14 and 15. Incidentally, a measuring instrument similar to the one used in Example 1 was used as the measuring instrument.

Focusing attention on FIG. 12, it can be seen that the impedance changes in the order of a, b, c, d, e, f, and g in correspondence with the compressive load applied repeatedly three times in the order of 0-4.46 tonf-0-4.46 tonf-0-4.46 tonf-0, and that the change in impedance is small when the compressive load is reduced. Accordingly, by detecting the change in impedance, it is possible to detect the application of a vertical force to the rubber member 13, i.e., the generation of the internal strain in the rubber member 13. In addition, by performing the integration and the like of the times the impedance changes, it is possible to detect the extent of the deterioration of the rubber member 13 ascribable to the generation of the repeated internal strain. As a result, it is possible to readily ascertain the extent of the deterioration of the rubber member 13 by introducing the lead wires to a remote place, e.g., a monitoring chamber or the like, and by monitoring the change in impedance there.

Figure 13:
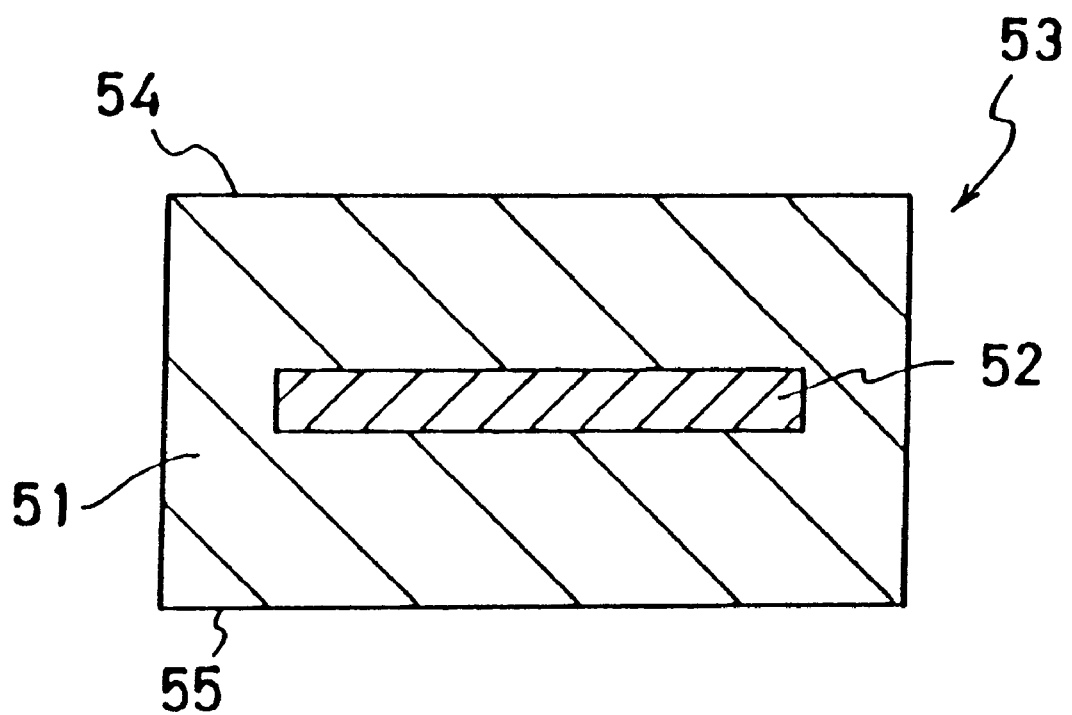
FIG. 13 is a cross-sectional view of another example of a rubber bearing to which the method of the present invention is applicable.

It should be noted that the method of the present invention is also applicable to, in addition to the rubber bearing 10 such as the one described above, a rubber bearing 53 comprised of a rubber member 51 and an inner steel plate 52 serving as a reinforcing member embedded in the rubber member 51, as shown in FIG. 13, by, for example, attaching electrodes to one end surface 54 of the rubber member 51 and the other end surface 55 opposed thereto, respectively.

We claim:

1. A method for detecting a deterioration of a rubber bearing which comprises a load supporting rubber member, a metal reinforcing member disposed in the rubber member, and flange plates respectively disposed on opposite end surfaces of the rubber member, wherein said method comprises the steps of:

disposing said rubber bearing in a lower portion of a building to receive a load from the building;

repeatedly measuring electrical impedance of the load supporting rubber member under normal stress states due to normal load from said building after external stresses have been repeatedly applied to the rubber bearing due to a change of said load from said building, to provide electrical impedance measurements of the rubber member under the normal stress states, respectively;

comparing a preceding electrical impedance measurement of the rubber member with a subsequent electrical measurement of the rubber member subsequent to said preceding electrical impedance measurement, the preceding electrical impedance measurement being a value under the normal stress state of the rubber bearing after a preceding external stress has been applied to the rubber bearing, the subsequent electrical impedance measurement being a value under the normal stress state of the rubber bearing after a subsequent external stress to said preceding external stress has been applied to the rubber bearing;

detecting changes of the subsequent electrical impedance measurement from the preceding electrical impedance measurement from a result of the comparison; and determining a deterioration of the rubber member based on said external stresses applied to the rubber bearing from a result of the detection.

2. A method according to claim 1, wherein the electrical impedance is measured through said reinforcing member as an electrode.

3. A method according to claim 1, wherein the electrical impedance is measured through said flange plates as electrodes.

4. A method according to claim 1, further comprising a step of integrating times of change of the electrical impedance measurement, said determining step further including determining deterioration of the rubber member based on said external stresses applied to the rubber bearing, in response to the integrated times of the electrical impedance measurements.

5. A method for detecting a deterioration of a rubber bearing which comprises a load supporting rubber member, a metal reinforcing member disposed in the rubber member, and flange plates respectively disposed on opposite end surfaces of the rubber member, wherein said method comprises the step of:

disposing said rubber bearing in a lower portion of a building to receive a load from the building;

repeatedly measuring electrical impedance of the load supporting rubber member under normal stress states due to normal load from said building before an external stress is applied to the rubber bearing and after external stresses have been repeatedly applied to the rubber bearing, due to a change of said load from said building, to provide electrical impedance measurements of the rubber member under the normal stress states, respectively;

repeatedly comparing an original electrical impedance measurement of the rubber member with subsequent electrical measurements of the rubber member subsequent to said original electrical impedance measurement, the original electrical impedance measurement being a value under the normal stress state of the rubber bearing before a first external stress is applied to the rubber bearing, the subsequent electrical impedance measurements being values under the normal stress state of the rubber bearing after the external stresses have been applied to the rubber bearing, respectively;

detecting changes of each of the subsequent electrical impedance measurements from the original electrical impedance from a result of the comparison; and determining a deterioration of the rubber member based on said external stresses applied to the rubber bearing from a result of the detection.

6. In combination, a rubber bearing having a load supporting rubber member, a metal reinforcing member disposed in the rubber member, and flange plates respectively disposed on opposite end surface of the rubber member, and an apparatus for detecting a deterioration of the rubber bearing, said rubber bearing being disposed in lower portion of a building to receive a load from the building, the apparatus including:

measuring means for repeatedly measuring electrical impedance of the load supporting rubber member under normal stress states due to normal load from said building before an external stress is applied to the rubber bearing and after external stresses have been repeatedly applied to the rubber bearing, due to a change of said load from said building, to provide electrical impedance measurements of the rubber member under the normal stress states, respectively;

comparing means for repeatedly comparing an original electrical impedance measurement of the rubber member from said measuring means with subsequent electrical measurements of the rubber member from said measuring means subsequent to said original electrical impedance measurement, the original electrical impedance measurement being a value under the normal stress state of the rubber bearing before a first external stress is applied to the rubber bearing, the subsequent electrical impedance measurements being values under the normal stress state of the rubber bearing after the external stresses have been applied to the rubber bearing, respectively;

detecting means for detecting changes of each of the subsequent electrical impedance measurements form the original electrical impedance from a result the comparison of said comparing means; and determining means for determining a deterioration of the rubber member based on said external stresses applied to the rubber bearing from a result of the detection of said detecting means.

\* \* \* \* \*

UNITED STATES PATENT AND TRADEMARK OFFICE
CERTIFICATE OF CORRECTION

PATENT NO.    : 5,999,004
DATED         : December 7, 1999
INVENTOR(S)   : Okawa et al.

It is certified that error appears in the above-identified patent and that said Letters Patent is hereby corrected as shown below:

<u>Title page,</u>
Item [73], should read:
-- [73]   Assignee:   Japan Atomic Energy Research Institute, Tokyo, Japan
                     Oiles Corporation, Tokyo, Japan --

Signed and Sealed this

Fourth Day of February, 2003

JAMES E. ROGAN
*Director of the United States Patent and Trademark Office*